United States Patent
Rensen et al.

(10) Patent No.: US 9,176,153 B2
(45) Date of Patent: Nov. 3, 2015

(54) PREVENTION THERAPY AND PROGNOSIS/MONITORING IN SEPSIS AND SEPTIC SHOCK

(75) Inventors: Patrick Cornelis Nicolaas Rensen, Leiden (NL); Aloysius Maria Havekes, Alpern aan den Rijn (NL)

(73) Assignee: NEDERLANDSE ORGANISATIE VOOR TOEGEPASTNATUURWETENS­CHAPPELIJK ONDERZOEK TNO, Delft (NL)

( * ) Notice: Subject to any disclaimer, the term of this patent is extended or adjusted under 35 U.S.C. 154(b) by 1843 days.

(21) Appl. No.: 10/519,417

(22) PCT Filed: Jun. 27, 2003

(86) PCT No.: PCT/NL03/00475
§ 371 (c)(1),
(2), (4) Date: Dec. 22, 2004

(87) PCT Pub. No.: WO2004/002518
PCT Pub. Date: Jan. 8, 2004

(65) Prior Publication Data
US 2006/0111283 A1 May 25, 2006

(30) Foreign Application Priority Data
Jun. 28, 2002 (NL) ..................................... 1020962

(51) Int. Cl.
| A61K 35/14 | (2015.01) |
| A61K 39/00 | (2006.01) |
| A61K 39/38 | (2006.01) |
| A01N 63/00 | (2006.01) |
| G01N 33/92 | (2006.01) |
| A61K 38/17 | (2006.01) |

(52) U.S. Cl.
CPC ............ *G01N 33/92* (2013.01); *A61K 38/1709* (2013.01)

(58) Field of Classification Search
CPC .................... A61K 3/555; A61K 2039/55516; C12N 15/11; C07K 1/00; C07K 4/00; C07K 5/00; C07K 9/00; C07K 14/775
See application file for complete search history.

(56) References Cited

U.S. PATENT DOCUMENTS 6,004,925 A * 12/1999 Dasseux et al. .................. 514/2

FOREIGN PATENT DOCUMENTS

| WO | WO99/16458 | * | 4/1999 |
| WO | WO 01/07946 | * | 10/2001 | ............. C07K 14/47 |

OTHER PUBLICATIONS

Lauer et al., (J. Biol. Chem 1988. vol. 263(15): 7277-7286).*

(Continued)

*Primary Examiner* — Ja'na Hines
(74) *Attorney, Agent, or Firm* — Norris McLaughlin & Marcus, P.A.

(57) ABSTRACT

The invention relates to the use of a peptide which binds to lipopolysaccharide (LPS) or lipoteichoic acid (LTA), for manufacturing a pharmaceutical composition for treating sepsis or septic shock, wherein the peptide comprises the amino acid sequence of apolipoprotein CI (apoCI) or a part thereof that comprises at least the amino acids of the C-terminal helix of apoCI. The use of human apoCI is preferred. The peptide can be administered clinically to patients who have sepsis or threaten to develop sepsis. Measurement of the apoCI content in blood can be utilized for determining the severity and prognosis of the course of the septic condition or for monitoring an anti-sepsis treatment.

15 Claims, 8 Drawing Sheets

Predictive value of the apoCI content in blood plasma for the chance of survival of sepsis time after hospitalization (days)

(56) References Cited

OTHER PUBLICATIONS

Oosten et al., (J. of Biol. Chem. 2001. vol. 276(23): 8820-8824).*
Quarfordt et al., (J. of Biological Chem. 1982. vol. 257(24): 14642-14647).*
Rozek et al., ( Biochemistry. 1995. vol. 34, pp. 7401-7408).*
Rozek et al., (Biochemistry 1995, vol. 34:7401-7408).*
Pajkrt et al., (J. of Experimental Medicine. 1996. vol. 184(5): 1601-1608).*
Gautier et al., (J. of Biol. Chem. 2000. vol. 275. pp. 37504-37509.*
Read et al., ( J. of Experimental Medicine. 1995. vol. 182(1): 267-272).*
Shulman et al., (J. Biol. Chem. 250, 182-190, 1975).*

* cited by examiner

Figure 1

Predictive value of the apoCI content in blood plasma for the chance of survival of sepsis

Figure 2

ApoCI shows strong binding to LPS, which is resistant to an electrophoretic field

Figure 3

The interaction of apoCI with LPS inhibits the interaction of an apoCI-specific antibody with apoCI

Figure 4

The binding of apoCI to LPS leads to monomerization of apoCI micelles

Figure 5

The rate and degree of LPS monomerization by mice plasma is determined by the apoCI concentration

Figure 6

Binding of LPS to human apoCI leads to a strongly reduced interaction with the liver, while the residence time of L

Figure 7

Binding of LPS to human apoCI leads to an intensified LPS-induced inflammatory response

Figure 8

Plasma apoCI levels are positively correlated with TNFα levels in patients developing endotoxemia during a heart operation with cardiopulmonary bypass

|  | time point 1 | | time point 2 | | time point 3 | |
| --- | --- | --- | --- | --- | --- | --- |
|  | R | P | R | P | R | P |
| ApoCI | | | | | | |
| all patients | 0.150 | 0.128 | 0.290 | 0.004* | 0.289 | 0.003* |
| LPS <5 pg/mL | 0.165 | 0.464 | 0.300 | 0.176 | 0.178 | 0.440 |
| LPS >5 pg/mL | 0.141 | 0.216 | 0.293 | 0.010* | 0.317* | 0.004* |
| ApoCIII | | | | | | |
| all patients | 0.090 | 0.364 | -0.145 | 0.152 | 0.005 | 0.960 |
| LPS <5 pg/mL | -0.044 | 0.846 | -0.020 | 0.931 | 0.070 | 0.764 |
| LPS >5 pg/mL | 0.121 | 0.289 | -0.159 | 0.168 | 0.008 | 0.947 |

SEQUENCE LISTING

<160> NUMBER OF SEQ ID NOS: 11

<210> SEQ ID NO 1
<211> LENGTH: 17
<212> TYPE: PRT
<213> ORGANISM: Artificial Sequence
<220> FEATURE:
<223> OTHER INFORMATION: human apoCI peptide

<400> SEQUENCE: 1

Met Arg Glu Trp Phe Ser Glu Thr Phe Gln Lys Val Lys Glu Lys Leu
1               5                   10                  15

Lys

<210> SEQ ID NO 2
<211> LENGTH: 57
<212> TYPE: PRT
<213> ORGANISM: Artificial Sequence
<220> FEATURE:
<223> OTHER INFORMATION: human apoCI peptide

<400> SEQUENCE: 2

Thr Pro Asp Val Ser Ser Ala Leu Asp Lys Leu Lys Glu Phe Gly Asn
1               5                   10                  15

Thr Leu Glu Asp Lys Ala Arg Glu Leu Ile Ser Arg Ile Lys Gln Ser
            20                  25                  30

Glu Leu Ser Ala Lys Met Arg Glu Trp Phe Ser Glu Thr Phe Gln Lys
        35                  40                  45

Val Lys Glu Lys Leu Lys Ile Asp Ser
    50                  55

<210> SEQ ID NO 3
<211> LENGTH: 23
<212> TYPE: PRT
<213> ORGANISM: Artificial Sequence
<220> FEATURE:
<223> OTHER INFORMATION: human apoCI peptide

<400> SEQUENCE: 3

Ser Ala Lys Met Arg Glu Trp Phe Ser Glu Thr Phe Gln Lys Val Lys
1               5                   10                  15

Glu Lys Leu Lys Ile Asp Ser
            20

<210> SEQ ID NO 4
<211> LENGTH: 7
<212> TYPE: PRT
<213> ORGANISM: Artificial Sequence
<220> FEATURE:
<223> OTHER INFORMATION: C-terminal part of human apoCI

<400> SEQUENCE: 4

Lys Val Lys Glu Lys Leu Lys
1               5

<210> SEQ ID NO 5
<211> LENGTH: 7
<212> TYPE: PRT
<213> ORGANISM: Artificial Sequence
<220> FEATURE:
<223> OTHER INFORMATION: LPS-binding sequence of LALF

<400> SEQUENCE: 5

Lys Trp Lys Tyr Lys Gly Lys

<210> SEQ ID NO 6
<211> LENGTH: 7
<212> TYPE: PRT
<213> ORGANISM: Artificial Sequence
<220> FEATURE:
<223> OTHER INFORMATION: LPS-binding sequence of LALF

<400> SEQUENCE: 6

Lys Ile Lys Glu Lys Leu Lys
1               5

<210> SEQ ID NO 7
<211> LENGTH: 57
<212> TYPE: PRT
<213> ORGANISM: Baboon
<220> FEATURE:
<221> NAME/KEY: SITE
<222> LOCATION: (1)..(57)
<223> OTHER INFORMATION: primary amino acid sequence of apoCI

<400> SEQUENCE: 7

Ala Pro Asp Val Ser Ser Ala Leu Asp Lys Leu Lys Glu Phe Gly Asn
1               5                   10                  15

Thr Leu Glu Asp Lys Ala Trp Glu Val Ile Asn Arg Ile Lys Gln Ser
            20                  25                  30

Glu Phe Pro Ala Lys Thr Arg Asp Trp Phe Ser Glu Thr Phe Arg Lys
        35                  40                  45

Val Lys Glu Lys Leu Lys Ile Asn Ser
    50                  55

<210> SEQ ID NO 8
<211> LENGTH: 62
<212> TYPE: PRT
<213> ORGANISM: Canis sp.
<220> FEATURE:
<221> NAME/KEY: SITE
<222> LOCATION: (1)..(62)
<223> OTHER INFORMATION: primary amino acid sequence of apoCI

<400> SEQUENCE: 8

Ala Gly Glu Ile Ser Ser Thr Phe Glu Arg Ile Pro Asp Lys Leu Lys
1               5                   10                  15

Glu Phe Gly Asn Thr Leu Glu Asp Lys Ala Arg Ala Ala Ile Glu Ser
            20                  25                  30

Ile Lys Lys Ser Asp Ile Pro Ala Lys Thr Arg Asn Trp Phe Ser Glu
        35                  40                  45

Ala Phe Lys Lys Val Lys Glu His Leu Lys Thr Ala Phe Ser
    50                  55                  60

<210> SEQ ID NO 9
<211> LENGTH: 62
<212> TYPE: PRT
<213> ORGANISM: Rattus sp.
<220> FEATURE:
<221> NAME/KEY: SITE
<222> LOCATION: (1)..(62)
<223> OTHER INFORMATION: primary amino acid sequence of apoCI

<400> SEQUENCE: 9

Ala Pro Asp Phe Ser Ser Ala Met Glu Ser Leu Pro Asp Lys Leu Lys
1               5                   10                  15

Glu Phe Gly Asn Thr Leu Glu Asp Lys Ala Arg Ala Ala Ile Glu His

```
                    20              25              30
Ile Lys Gln Lys Glu Ile Met Ile Lys Thr Arg Asn Trp Phe Ser Glu
                35              40              45

Thr Leu Asn Lys Met Lys Glu Lys Leu Lys Thr Thr Phe Ala
            50              55              60

<210> SEQ ID NO 10
<211> LENGTH: 62
<212> TYPE: PRT
<213> ORGANISM: Muss p.
<220> FEATURE:
<221> NAME/KEY: SITE
<222> LOCATION: (1)..(62)
<223> OTHER INFORMATION: primary amino acid sequence of apoCI

<400> SEQUENCE: 10

Ala Pro Asp Leu Ser Gly Thr Leu Glu Ser Ile Pro Lys Leu Lys
1               5               10              15

Glu Phe Gly Asn Thr Leu Glu Asp Lys Ala Arg Ala Ala Ile Glu His
                20              25              30

Ile Lys Gln Lys Glu Ile Leu Thr Lys Thr Arg Ala Trp Phe Ser Glu
                35              40              45

Ala Phe Gly Lys Val Lys Glu Lys Leu Lys Thr Thr Phe Ser
            50              55              60

<210> SEQ ID NO 11
<211> LENGTH: 15
<212> TYPE: PRT
<213> ORGANISM: Artificial Sequence
<220> FEATURE:
<223> OTHER INFORMATION: human apoCI peptide

<400> SEQUENCE: 11

Met Arg Glu Trp Phe Ser Glu Thr Phe Gln Lys Val Lys Glu Lys
1               5               10              15
```

PREVENTION THERAPY AND PROGNOSIS/MONITORING IN SEPSIS AND SEPTIC SHOCK

FIELD OF THE INVENTION

The invention is in the field of medicine, more particularly the field of prognosis, prevention and therapy of sepsis and septic shock. The invention provides means for therapeutic prevention and treatment of sepsis and septic shock, as well as means to determine the severity of a septic condition and to make a prognosis for the further course, and means for septic monitoring of the course of a treatment of sepsis and septic shock.

BACKGROUND OF THE INVENTION

Sepsis and Septic Shock.

A normal bacterial inflammation is a highly regulated process whereby the defense system clears up bacteria. In humans with a weakened defense, the bacterium gets, an opportunity to proliferate (virtually uninhibitedly) and to break through to the blood stream. The presence of bacteria in the blood stream is called sepsis. Sepsis leads to the production of proinflammatory mediators by white blood cells (morkocytes and macrophages) in the blood. This reaction is crucial for a fast and efficient elimination of bacteria. However, if the inflammatory reaction persists too long, for instance due to disease-related immune suppression, this may eventually lead to severe fever, spontaneous blood clotting and damage of tissues due to oxygen deficiency and due to bactericidal products. In serious cases, organs (specifically kidney, heart and liver) may stop functioning and the patient may get into so-called septic shock, from which he may subsequently die.

Incidence.

In the United States alone, more than 500,000 patients a year develop septic shock, with an estimated incidence increase of about 1.5% a year, and the costs amount to $16.7 billion a year (Angus, 2001). Septic shock results in death in 20-80% of cases (depending on the definition used). The increasing use of invasive surgical techniques, chemotherapy and the application of immunosuppression in patients with organ transplants or inflammatory diseases constitute causes of an increasing number of cases of sepsis. The longer life expectancy of elderly people and patients having metabolic, neoplastic and immunodeficiency defects owing to improved medical care, also leads to populations at increased risk of bacterial infection.

Lipopolysaccharide and Lipoteichoic Acid.

Sepsis and septic shock are caused chiefly by Gram-negative bacteria (for instance *E. coli* and *K. pneumoniae*) and (to a lesser extent) Gram-positive bacteria (*S. aureus* and *S. epidermidis*).

Lipopolysaccharide (LPS) is the most important constituent of the outer membrane of Gram-negative bacteria. LPS is the most reactive component of Gram-negative bacteria. LPS activates mononuclear cells (monocytes and macrophages), after which these cells produce proinflammatory mediators such as cytokines (TNFα, IL-1.beta. IL-6) and oxygen radicals. This response is necessary for a fast and effective dealing with the bacterial infection, and plays a crucial role in the clearing up of the bacteria (Heumann, 2002). However, in case of an inadequate response, allowing the bacteria to continue to proliferate uninhibitedly, these mediators are responsible for the metabolic changes that lead to pathologic conditions and eventually to death, as demonstrated in rabbits, monkeys and mice.

The equivalent of LPS in Gram-positive bacteria is lipoteichoic acid (LTA), which possesses a structure that exhibits strong homology to that of LPS.

Current Clinical and Experimental Therapies.

The complexity of sepsis and the immunological defense render the development of pharmacological interventions more difficult. The standard treatment often consists in the administration of fluid and blood pressure raisers (so-called vasopressors) to normalize the blood pressure and the oxygen supply of organs, and antibiotics to inhibit the proliferation of bacteria (Rackow, 1991; Cohen, 1991; Wheeler, 1999), but this treatment is not sufficient to prevent the high mortality.

Most applied experimental strategies for treating sepsis have been aimed at inhibiting the proinflammatory response, for instance through capturing LPS, blocking the cytokine action or overall immune suppression.

However, various clinical studies have shown that LPS-neutralizing antisera are not effective in septic shock (Cohen, 1999). Likewise, experimental therapies with antibodies to inter alia TNFα (Fisher, 1996; Clark, 1998) and the IL-1 receptor (Fisher, 1994; Opal, 1997) proved not to be effective.

By means of a meta-analysis, it has been demonstrated that overall immune suppression increases the mortality resulting from sepsis (Cronin, 1995). A recent study in humans demonstrates that a polymorphism in the LPS receptor Toll-like receptor 4 (TLR4), which leads to a reduced inflammatory response against LPS, is associated with an increased sensitivity to severe bacterial infection (Kiechl, 2002). Furthermore, it is known that mice, which are deficient for the proinflammatory cytokine macrophage migration inhibitory factor (MIF), are less well capable of clearing up bacteria such as. *Leishmania major* (Satoskar, 2001) and *Salmonella typhimurium* (Koebernick, 2002).

Many suggestions have been made for treating sepsis or septic shock, all of which have in common that an LPS-binding peptide is administered to sepsis patients. The administration of these LPS binding peptides is typically aimed at the suppression of the LPS-induced activation of the immune system. The peptides to be administered can, for instance, be derived from LBP (LPS Binding Protein; see WO 95/25117), apoA and apoE (WO 98/07751), apoA1 (WO 95/25786; WO 99/16458; WO 99/16459; WO 99/16408; WO 99/16409), CAP18 (Larrick, 1994), CAP37 (U.S. Pat. No. 6,107,460; U.S. Pat. No. 5,650,392; U.S. Pat. No. 5,627,262; U.S. Pat. No. 5,607,916), CD14 (WO 96/20956), prophenin (WO 95/34289; WO 95/26747), polyphemusin (WO 02/00687) and LALF protein (U.S. Pat. No. 5,747,455). To date, however, all of these suggestions have not yielded an effective approach for sepsis and septic shock either.

Sepsis has great consequences for the lipoprotein metabolism. Patients who get to the clinic exhibit strongly lowered cholesterol levels in the blood, which normalize after successful antibacterial therapy. Research in vitro and in experimental animals has demonstrated that lipoproteins can offer protection against sepsis, but the complexity of lipoproteins (including composition, endogenous character) makes their clinical application more difficult. Also, the mechanism by which lipoproteins play a protective role is still unknown. It has been reported that infusion of protein-free triglyceride-rich lipid emulsions does not afford protection (Van der Poll, 1995), which indicates that it is precisely the protein components of lipoproteins that can play a large protective role in sepsis.

BRIEF DESCRIPTION OF THE INVENTION

An object of the invention is to provide a prevention or effective handling (therapeutic treatment) of sepsis and septic shock, which is more efficient than the treatment methods proposed heretofore and/or avoids disadvantages thereof.

Another object of the invention is to provide means and methods by which the proinflammatory reaction as induced by the toxic components of bacteria, in particular LPS and/or LTA, in septic patients can be enhanced.

A further object of the invention is to provide a reliable determination of the severity of a septic condition and reliable prognosis of sepsis or septic shock.

A still further object of the invention is to provide a reliable evaluation of the pathologic condition of septic patients, so that the effect of a treatment of the disease can be measured.

To that end, the invention provides the use of a peptide which binds to lipopolysaccharide (LPS) or lipoteichoic acid (LTA), for manufacturing a pharmaceutical composition for treating sepsis or septic shock, the peptide comprising the amino acid sequence of apolipoprotein CI (apoCI) or a part thereof that comprises at least the amino acids of the C-terminal helix of apoCI.

In particular, this concerns a peptide which comprises the amino acid sequence of human apoCI or a part thereof that comprises at least the amino acids of the C-terminal helix of human apoCI. However, apoCI of a non-human mammal, or a corresponding fragment thereof, can also be used. For applications in, e.g., domestic animals, such as horse, cow, dog and cat, typically the use of an apoCI of the respective mammal will be preferred.

Most preferred according to the invention, however, is that the peptide is human apoCI or a fragment thereof that comprises at least the amino acids MREWFSETFQKVKEKLK, SEQ ID NO.:1.

Concretely, the peptide is preferably human apoCI having the amino acid sequence TPDVSSALDKLKEFGNTLED-KARELISRIKQSELSAKMREWFSETFQKVKEKLKIDS, SEQ ID NO.:2. However, it is also possible to use a fragment, for instance the peptide SAKMREWFSETFQKVKEK-LKIDS, SEQ ID NO.:3 or the peptide MREWFSET-FQKVKEKLK, SEQ ID NO.:1.

In particular, this concerns the use of a peptide which binds to lipopolysaccharide (LPS), as defined herein, whereby a pharmaceutical composition is manufactured for preventing or treating a sepsis or septic shock caused by Gram-negative bacteria in mammals, in particular humans or a domestic animal, such as horse, cow, dog and cat.

However, the invention also comprises the use of a peptide that binds to lipoteichoic acid (LTA), as defined herein, whereby a pharmaceutical composition is manufactured for preventing or treating a sepsis or septic shock caused by Gram-positive bacteria in mammals, in particular humans or a domestic animal, such as horse, cow, dog and cat.

Also, according to the invention, there is provided a pharmaceutical composition for preventing or treating sepsis or septic shock, which composition comprises a peptide as defined herein, as well as a pharmaceutically acceptable carrier.

Further, the invention provides a method for preventively treating a mammal, in particular human individual, which, for instance as a result of a surgical intervention or a weakened or deficient immune system, is at increased risk of developing sepsis, wherein an active amount of a peptide as defined herein is administered to the mammal.

Likewise, the invention provides a method for treating a mammal, in particular human individual, which suffers from sepsis or septic shock, wherein an active amount of a peptide as defined herein is administered to the mammal.

Also, the invention provides a method for determining the severity of a septic condition and making a prognosis for the further course of the sepsis or septic shock in a mammal, in particular human individual, which is suffering from sepsis or septic shock, wherein the apoCI content in a blood sample of the mammal is determined.

Likewise, the invention provides a method for monitoring a treatment of sepsis or septic shock in a mammal, in particular human individual, which is being treated for sepsis or septic shock, wherein the apoCI content in a blood sample of the mammal is determined.

DETAILED DESCRIPTION OF THE INVENTION

Role of apoCI in Sepsis.

Figure 1:
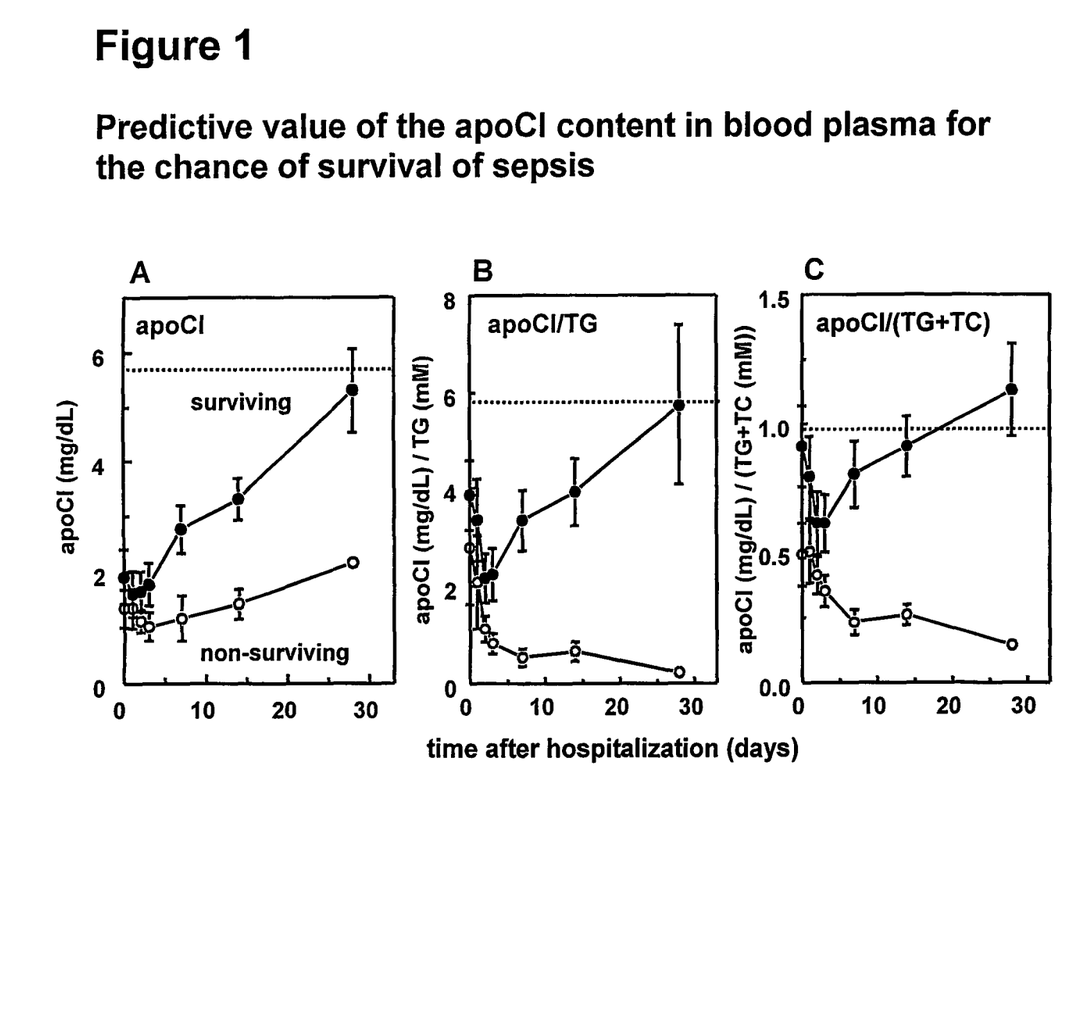
FIG. 1 shows the relation between the apoCI level in the blood plasma of sepsis patients and the lapse of time after admission to the clinic. The figure demonstrates the predictive value of the apoCI level for the chance of survival of sepsis.

We have found, as Example 1 and FIG. 1 show, that the level (the concentration) of apolipoprotein CI (apoCI) in septic blood is strongly lowered, which does not hold, or holds to a much lesser extent, for the (numerous) other apolipoproteins. This lowered apoCI content in septic blood is confirmed by the literature (Barlage, 2001), although the authors have not discussed a possible role of apoCI in sepsis.

ApoCI is the smallest apolipoprotein (6.6 kDa, 57 amino acids) which is chiefly synthesized by the liver and circulates in the blood in a fairly high concentration (.about.6 mg/dL), both in free, unbound form and as a constituent of lipoproteins (chylomicrons, VLDL, HDL) (Jong, 1999). The amino acid sequence of apoCI is known (see Table 1). To date, no mutations have become known that lead to different variations ('polymorphisms') of apoCI. Using transgenic mice that overexpress the human apoCI, we have demonstrated that apoCI plays a role in the lipid metabolism, since apoCI overexpression leads to increased lipid levels in the blood (Jong, 1996; Jong, 1998), but a role, if any, of apoCI in sepsis was not yet known.

We have developed the hypothesis that the apoCI depletion associated with sepsis is a direct consequence of bacterial infection. The low apoCI concentration might be the consequence of binding of apoCI to bacterial products, specifically LPS, which may possibly lead to accelerated clearance of apoCI from the blood.

Via an extensive literature study, it was found that LPS-binding proteins have common characteristics, with the presence of a combination of positively charged and hydrophobic amino acids being essential. Two of these proteins are the limulus anti-LPS factor (LALF) (Hoess, 1993), a factor in the 'LAL assay' routinely used to measure the LPS activity, and CAP18 Larrick, 1994), which is synthesized by polymorphonuclear cells.

In fact, apoCI contains a large number of positively charged lysines (one in each six amino acids), alternated with hydrophobic amino acids. To our surprise, human apoCI contains a peptide sequence in its C-terminal portion (KVKEKLK) SEQ ID NO.:4 which is virtually identical to the LPS-binding sequences of LALF (KWKYKGK) SEQ ID NO.:5 and CAP18 (KIKEKLK), SEQ ID NO.:6 where symbols in bold-type and italics respectively represent positively charged and hydrophobic amino acids. We have subsequently demonstrated that apoCI, both in pure form and as a constituent of plasma in fact binds strongly to LPS (see Example 2 and FIGS. 2, 3, 4 and 5).

We have compared the amino acid sequences of apoCI, such as occur in man (SwissProt P02654), baboon (SwissProt P34929), dog (SwissProt P56595), rat (SwissProt P19939) and mouse (SwissProt P34928), as can be found under the numbers indicated (http://www.expasy.ch/sprot/). See Table 1.

The consensus LPS-binding sequence underlined in Table 1 as found in human apoCI (KVKEKLK) SEQ ID NO:4 has been found to occur virtually unmodified in the animal variants. Human apoCI forms two amphipatic helices of class 2 (amino acid sequences 7-29 and 38-52), which facilitate the binding of apoCI with lipoproteins. On the basis of structural homology, it is assumed that animal apoCI takes a comparable structure.

Working Mechanism of apoCZ.

On the basis of the disappointing results of the earlier discussed, failing experimental antiseptic therapies, we have furthermore developed the hypothesis that therapeutic reduction of the proinflammatory response is not only ineffective but even undesirable, because in this way the causative bacterial proliferation is not inhibited. Although the cause of sepsis is very heterogeneous and the time of intervention may be determinative of the success of the treatment, we deem it likely that specifically enhancement of the inflammatory response in an early stage of sepsis increases the antibacterial effectiveness and hence raises the chance of survival.

While proteins, such as CAP18, LALF, CAP37, prophenin and polyphemusin, which do not form part of lipoproteins, are also capable of binding LPS, they do not, in contrast with apoCI, occur in a high concentration in the blood. Further, these proteins lead to suppression of the LPS-related inflammation cascade, which according to our hypothesis is unfavorable for the course of the disease. The bacterial infection will, as a result, aggravate rather than improve.

Surprisingly, we have now established that the binding of LPS to human apoCI leads to a considerably longer residence time of LPS in the blood (see Example 4 and FIG. 6), owing to its binding to plasma lipoproteins, facilitated by the amphiphilic structure of apoCI. Also, we have established that administration of LPS with apoCI to mice leads to a strongly increased proinflammatory response compared with mice that were administered LPS alone, which appears from a fourfold increased TNFα production (see Example 5 and FIG. 7). The finding that apoCI enters into a direction interaction with LPS is new and points to a direct role of apoCI in the endogenous control of bacterial sepsis.

Because apoCI is a constituent of lipoproteins (chylomicrons, VLDL and HDL) and is consequently cleared slowly from the blood, we therefore suppose that the binding of LPS to apoCI extends the residence time of LPS in the blood, so that the activation of white blood cells is additionally stimulated in a natural way. As a result, the production of proinflammatory cytokines (TNFα, IL-1β and IL-6) will increase and consequently the antibacterial inflammation cascade will work extra strongly. This mechanism can also partly explain why lipoproteins play a protective role in sepsis. Accordingly, the essence of the present invention is that through administration of apoCI, or an adequate fragment thereof, as defined herein, a timely, extra forceful inflammation cascade is

TABLE 1

Primary amino acid sequences of apoCI.

| | |
|---|---|
| Human apoCI (1-57) | |
| TPDVSSALDKLKEFGNTLEDKARELISRIKQSELSAKMREWFSETFQKVKEKLKIDS | SEQ ID NO.: 2 |
| Baboon apoCI (1-57) | |
| APDVSSALDKLKEFGNTLEDKAWEVINRIKQSEFPAKTRDWFSETFRKVKEKLKINS | SEQ ID NO.: 7 |
| Dog apoCI (1-62) | |
| AGEISSTFERIPDKLKEFGNTLEDKARAAIESIKKSDIPAKTRNWFSEAFKKVKEHLKTAFS | SEQ ID NO.: 8 |
| Rat apoCI (1-62) | |
| APDFSSAMESLPDKLKEFGNTLEDKARAAIEHIKQKEIMIKTRNWFSETLNKMKEKLKTTFA | SEQ ID NO.: 9 |
| Mouse apoCI (1-62) | |
| APDLSGTLESIPDKLKEFGNTLEDKARAAIEHIKQKEILTKTRAWFSEAFGKVKEKLKTTFS | SEQ ID NO.: 10 | obtained which enables early neutralization of both LPS and the LPS-producing bacteria, so that the stage of full-blown sepsis or septic shock will not be reached.

Clinical Applicability.

The small size of apoCI enables obtainability of the protein on a large scale through so-called solid-phase peptide synthesis. This holds to a greater extent for smaller peptides (fragments of apoCI), which bind LPS and stimulate LPS-induced activation of white blood cells. Since apoCI is an endogenous plasma protein, it will be tolerated well and not generate any (additional) immune reactions. (For that reason, use of human apoCI will be preferred in humans, while in animals, preferably the corresponding animal apoCI will be used).

It is noted that according to the invention, apoCI, or a suitable fragment thereof, is used as the active substance to control or prevent sepsis or septic shock. According to the invention, the apoCI is not used as carrier for another substance. According to the invention, the apoCI, or fragment thereof, is preferably used as free peptide, not bound in complexes with lipids.

Measurement of apoCI Content for Prognosis or Monitoring.

As is demonstrated in Example 1 and FIG. 1, patients having severe sepsis exhibit a strongly lowered apoCI level. In the example given (17 patients admitted to the clinic with severe sepsis) the apoCI level was on average 1.6 mg/dL. The apoCI levels in patients who eventually survived the sepsis (47%: 8/17) exhibited a progressive rise after 3 days and normalized after about 4 weeks. By contrast, the apoCI levels in the patients who eventually died from the sepsis within 4 weeks (53%: 9/17), did not exhibit any rise. These data show that monitoring of the apoCI concentration in blood plasma has a prognostic value for the chance of survival of the septic patient (see also FIG. 1), and can be used for monitoring the effect of antiseptic therapies.

A. The Peptides to be Used According to the Invention.

As set out above, the invention comprises the application of apoCI and peptides derived therefrom which bind to LPS for the therapeutic treatment of Gram-negative bacterial sepsis. However, since apoCI and peptides derived therefrom also bind to lipoteichoic acid (LTA), the toxic equivalent of LPS in Gram-positive bacteria, the invention comprises the use of apoCI in bacterial infections in general, hence also in Gram-positive bacterial sepsis.

According to a particular preferred embodiment, the peptide consists of the whole amino acid sequence of apoCI (or comprises this sequence), in particular that of human apoCI, which consists of 57 amino acids according to the amino acid sequence TPDVSSALDKLKEFGNTLEDKARELIS-RIKQSELSAKMREWFSETFQKVKEKLKIDS, SEQ ID NO.:2

According to another preferred embodiment, the peptide is, or comprises, the amino acid sequences of homologues of human apoCI such as they occur in the animal kingdom (in particular in mammals, for instance horse, cow, dog, rabbit, rat, mouse).

According to another preferred embodiment, the peptide is, or comprises, at least the C-terminal helix of apoCI. In human apoCI, the C-terminal helix is formed by the amino acids 38-52, with the amino acid sequence MREWFSET-FQKVKEK, SEQ ID NO.:11. Preferably, a useful fragment of human apoCI comprises at least the amino acids MREWF-SETFQKVKEKLK, SEQ ID NO.:1. Examples of suitable peptides are, for instance, the peptides MREWFSET-FQKVKEKLK, SEQ ID NO.:1 and SAKMREWFSET-FQKVKEKLKIDS, SEQ ID NO.:3. These peptides comprise the C-terminal helix of apoCI and the whole putative LPS binding sequence KVKEKLK, SEQ ID NO.:4. Instead of a fragment of human apoCI, a corresponding fragment of an animal apoCI can be used.

A property important according to the invention of apoCI and the peptides defined herein, is, besides their binding to LPS, their binding to lipoproteins.

B. Obtaining the Peptides.

The complete human apoCI protein (amino acids 1-57) is commercially available (BIODESIGN International, Maine, USA and INTRACEL Corporation, Maryland, USA). Also, procedures have been described to isolate human apoCI as pure protein from blood (Tournier, 1984; Jackson, 1986). Finally, there is the possibility of constructing an adenoviral expression vector that codes for human or animal apoCI, so that apoCI can be produced on a large scale by astrocytoma cells in culture (Kypreos, 2001). Because apoCI is a very small protein, there is also the possibility of obtaining it from the individual amino acids by means of solid phase peptide synthesis (Clark-Lewis, 1986). This technique also enables systemization of all human apoCI analogs and other apoCI-derived peptides as described herein.

C. Administration Forms and Routes.

Human apoCI is water-soluble and so can be administered intravenously in an aqueous solution (for instance in a physiological saline solution). Single-time (bolus) injection is a possibility, as is continuous infusion.

Also, apoCI has lipid-binding properties, which further permits intravenous administration as a constituent of commercially available triglyceride-rich lipid emulsions (e.g. Intralipid®, Intrafat® and Lipofundin®) which are clinically routinely used as efficient parenteral energy source. In this case, too, bolus injection and continuous infusion both are possibilities.

All this likewise holds for the peptides according to the invention.

Oral administration of peptides according to the invention and of apoCI in particular is in principle also possible (Buclin, 2002).

Pharmaceutically acceptable carriers that are suitable for these different administration routes are naturally known to those skilled in the art.

D. Therapeutic Dose.

The plasma concentration of apoCI in healthy individuals is on average 6 mg/dL (Curry, 1981), while we have demonstrated that apoCI in septic patients is strongly lowered. It is expected that a plasma concentration of 0.05-500 mg/dL (preferably 0.5-50 mg/dL) can be therapeutically effective.

Based on an average plasma volume of 2.5 L given a body weight of 70 kg, it can be calculated that a dose of 0.02 mg/kg-200 mg/kg (preferably 0.2 mg/kg-20 mg/kg) can be effective in the case of a single-time (bolus) injection.

When administered as infusion, the dose will be strongly dependent on the rate of clearance of the apoCI from the blood, so that the dosing can vary within wide limits, for instance from 0.01 to 10 mg/kg/minute.

E. Expected Effect of the Treatment.

It is expected that apoCI will bind freely circulating LPS and LTA and will keep them present in the blood longer, so that LPS and LTA will be able to induce an increased proinflammatory antibacterial reaction, so that bacteria and LPS are neutralized faster and more effectively. Both preventive application of apoCI in individuals at increased risk of developing sepsis (for instance in the case of major surgery, or with immune deficiency) and application of apoCI in sepsis or septic shock will lead to the prevention of death resulting from sepsis.

F. Prognosis and Monitoring of Sepsis or Septic Shock.

The apoCI level in blood plasma can be established in any suitable manner. Preferably, the apoCI level is determined with a sandwich Enzyme-Linked ImmunoSorbent Assay (sandwich ELISA). To this end, for instance 96-wells plates (medium-binding plates; Costar) are coated with a (10,000-fold dilution of a) polyclonal antibody to human apoCI generated in goat (goat-anti human apoCI; Academy Bio-Medical Company, Houston, USA; cat. 31A-G1b). Next, human blood plasma or serum is added (100,000-300,000-fold dilution), whereby the apoCI present therein is quantitatively bound by this primary antibody. The apoCI is recognized by a secondary antibody (15,000-fold dilution) which is coupled to horseradish peroxidase (HRP) (HRP-goat-anti human apoCI; Academy Bio-Medical Company, Houston, USA; cat. 31H-G1b). The HRP is subsequently quantified by means of a stain reaction with 3,3',5,5'-tetramethylbenzidine (TMB) as substrate, and the stain intensity is compared with a calibration curve which is constructed with pure human apoCI (Labconsult, Brussels, Belgium; cat. A50366H).

Those skilled in the art, of course, know many variants of this apoCI determination. Thus, other assay techniques than ELISA can be used, other detection systems (enzymes and substrates), etc.

EXAMPLES

The finding that apoCI (and peptides derived therefrom) play a protective role in Gram-negative (and Gram-positive) sepsis is supported by a number of experiments. To that purpose, use is made of:
 a. blood of septic patients;
 b. mice that do not synthesize apoCI (apocl.sup.−/− mice);
 c. transgenic mice that overexpress human apoCI (APOC1 mice);
 d. apoCI which has been purified from human blood.

The findings are described in the Examples given hereinbelow.

Example 1

Predictive Value of the apoCI Level for the Chance of Survival in Sepsis

We have measured the apoCI levels in the blood plasma of 17 septic patients for-four weeks after admission to the clinic. For that purpose, we used the human-apoCI-specific sandwich ELISA as described above under F.

The results are shown in FIG. 1.

Of the 17 septic patients who were admitted to the clinic with severe sepsis, blood samples were taken over a period of 28 days. In the blood plasma, the contents of apoCI, triglycerides (TG) and total cholesterol (TC) were measured.

In FIG. 1A the apoCI content is plotted against time. In FIG. 1B the apoCI content has been corrected for the triglyceride content as a measure for the amount of triglyceride-rich lipoproteins, and in FIG. 1C the apoCI content has been corrected for both triglycerides and cholesterol as a measure for the total amount of circulating lipoproteins. A distinction was made between the patients who survived the sepsis (closed symbols; n=9.+−.SEM) and the patients who died from the sepsis within 30 days (open symbols; n=8+SEM). The dotted lines indicate the values as found in healthy individuals.

All patients who were included in the investigation exhibited a strongly lowered apoCI level in the blood (ca. 1.6 mg/dL). The patients who died from the consequences of sepsis within four weeks, exhibited a lower apoCI level (ca. 1.3 mg/dL) at the time of admission than did the patients who survived the sepsis (ca. 1.9 mg/dL). While the apoCI level virtually normalized within four weeks in patients who survived the sepsis (ca. 5 mg/dL), the apoCII level did not exhibit any rise in the patients who eventually died from sepsis.

These data show that the plasma level of apoCI has a predictive value for the chance of survival in sepsis. Also, they underline our hypothesis that apoCI falls short in patients who die from sepsis, and which can therefore have a therapeutic use.

Example 2

Purified apoCI Binds Strongly to LPS

In this Example, it is demonstrated that purified human apoCI binds strongly to LPS and that this binding is resistant to electrophoretic forces (agarose gel electrophoresis). It was found this involved the loss of the naturally occurring micellary structure of LPS.

Figure 2:
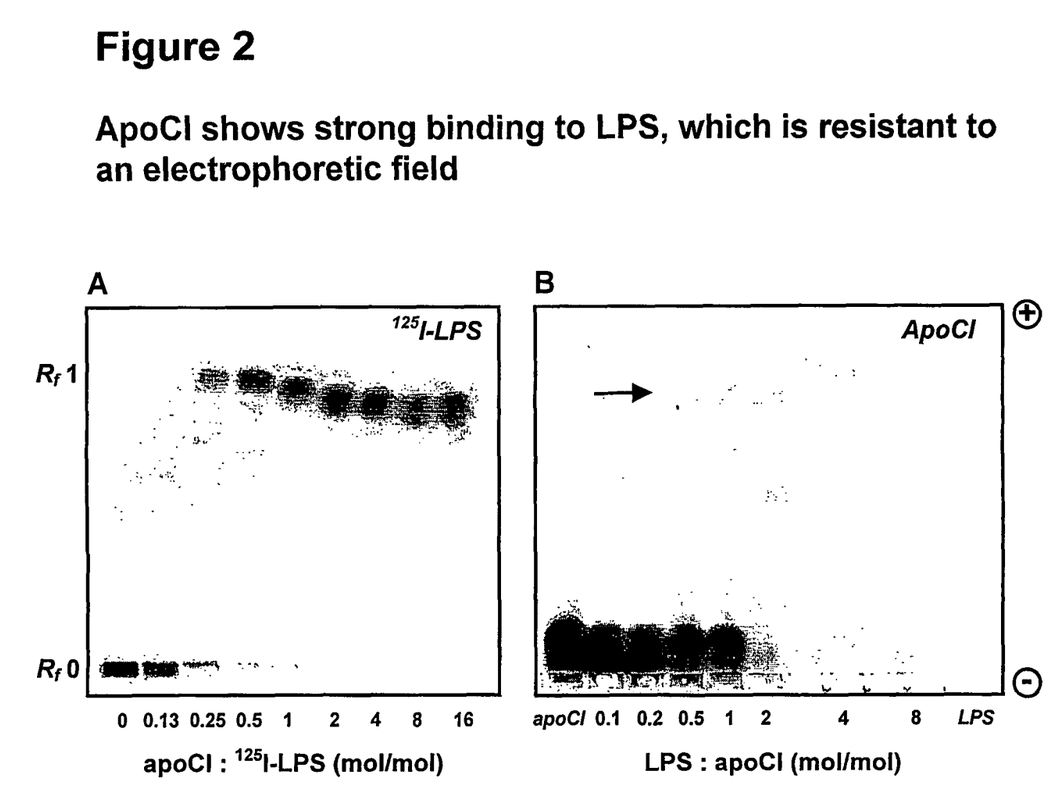
FIG. 2 shows the effect of an electrophoretic field on the migration of apoCI and/or LPS through an agarose matrix. The figure demonstrates a physical interaction between apoCI and LPS, which leads to comminution of LPS aggregates and also to reduced recognition of apoCI by a specific antibody.
Figure 3:
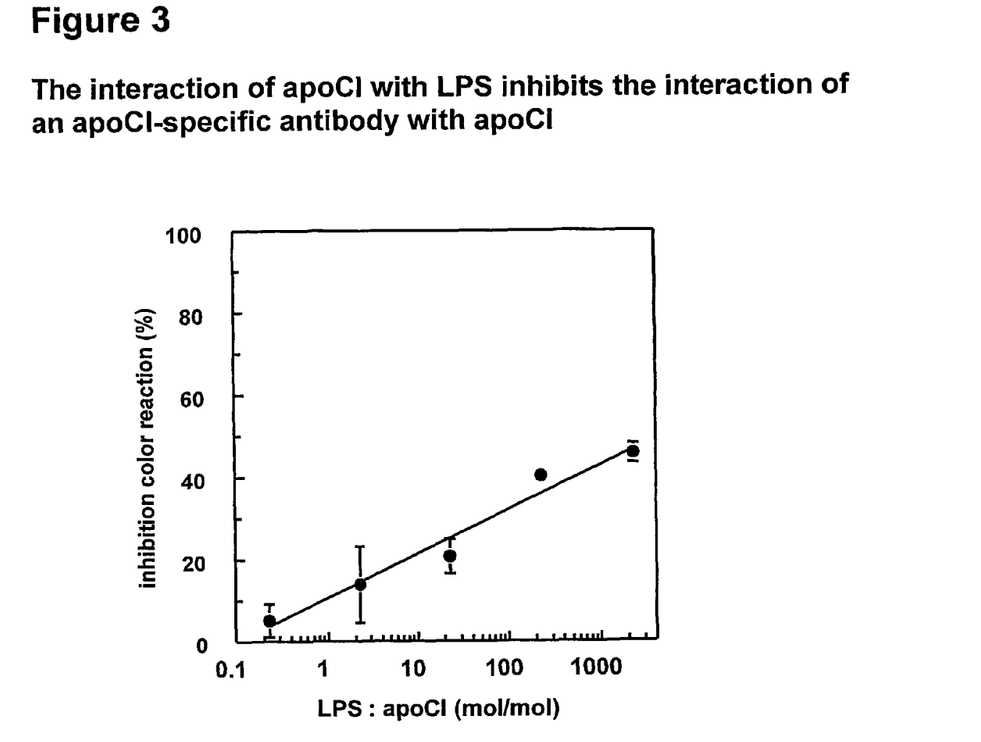
FIG. 3 shows the relation between the molar LPS:apoCI ratio and the inhibition of the stain reaction during ELISA by which the concentration of apoCI is determined. The figure shows a strong interaction between apoCI and LPS, which can prevent the binding of a specific antibody to apoCI.
Figure 4:
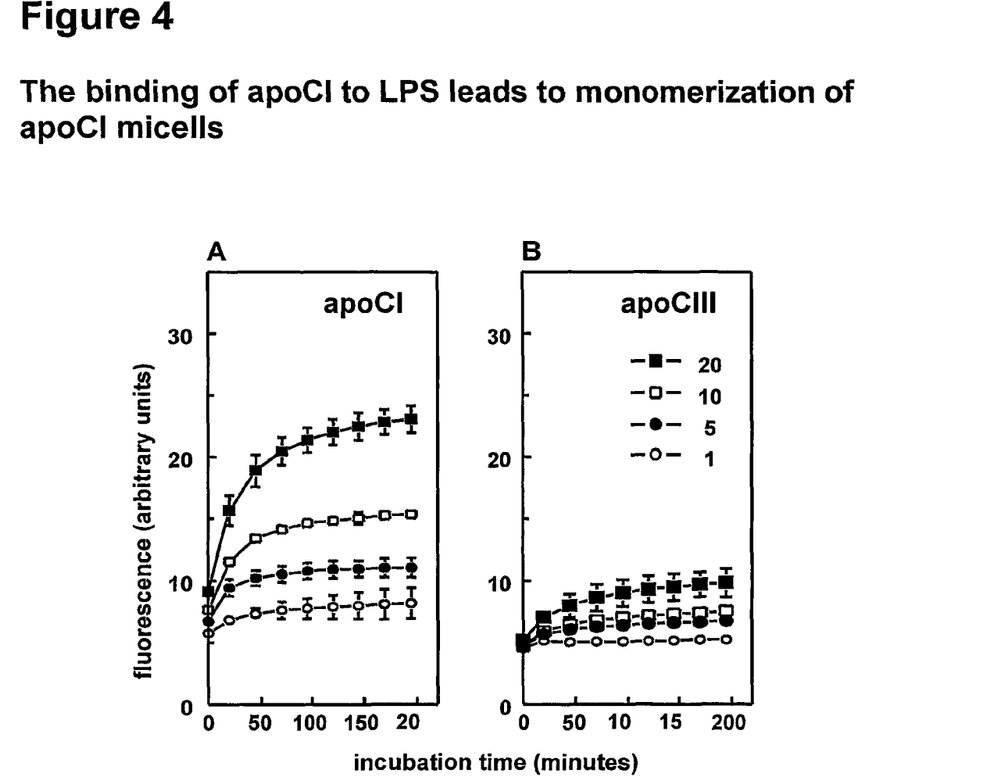
FIG. 4 shows the effect of apoCI and apoCIII on the time-dependent deaggregation of LPS. The figure shows a dose-dependent monomerization of LPS micelles by apoCI, while apoCIII is hardly effective.

The results are shown in FIGS. 2, 3 and 4.

LPS Re595 (*Salmonella minnesota*) was radioactively labeled with $^{125}$I as described (Rensen, 1997) and incubated (30 min at 37° C.) with increasing amounts of human apoCI which has been isolated from human blood (Tournier, 1984). Next, the incubation volumes were transferred to an agarose gel (position $R_f 0$), after which, for 2 hours, an electrophoretic field was applied (so-called agarose gel electrophoresis). After electrophoresis, the $^{125}$I-LPS was visualized by means of autoradiography. Through its negative charge, LPS tends to migrate to the positive pole (anode); which, however, is prevented in that the LPS forms large micellary structures that cannot pass the relatively small pores formed by the agarose matrix. However, addition of a small amount of apoCI (only 0.5 molecules of apoCI with respect to 1 molecule of LPS) already led to complete migration of the LPS to the positive pole, which indicates that apoCI binds to LPS thereby forming relatively small apoCI/LPS complexes (FIG. 2A);

Also, the effect of increasing amounts of LPS on the migration of a fixed amount of apoCI was determined. For that purpose, the apoCI was visualized in the gel after electrophoresis by means of immunoblotting with a horseradish peroxidase-conjugated antibody directed against human apoCI (Academy Bio-Medical Company, Houston, USA; cat. 31H-G1b). The binding of LPS to apoCI led to accelerated migration of apoCI to the positive pole, which indicates that apoCI in effect enters into a physical interaction with LPS (FIG. 2B) The affinity of the binding of LPS to apoCI proves to be so high that LPS prevents demonstration of apoCI during immunoblotting of the agarose gel with the apoCI-specific antibody in a dose-dependent manner (FIG. 2B).

A particular amount of human apoCI (0.75 ng/mL) was incubated with LPS in increasing molar ratios, after which the apoCI concentration was determined with the aid of the human apoCI-specific sandwich ELISA as described above under F. The LPS-induced inhibition of the stain reaction from which the apoCI concentration is read, was determined as a percentage of the maximum staining in the absence of LPS (n=2.+−.SEM) (FIG. 3). Again, the binding of LPS to apoCI proved to prevent the reaction of apoCI with the apoCI-specific antibody in a dose-dependent manner. Addition of a 200-fold molar excess of LPS to apoCI led to more than 40% inhibition of the staining reaction, that is, a nearly twofold underestimation of the apoCI concentration. Although apoCIII has a size (79 amino acids) and structure (two amphipatic helices) equal to apoCI, LPS had no effect on the quantification of concentrations of apoCIII with the aid of a comparable apoCIII-specific sandwich ELISA (FIG. 3).

Finally, the effect of apoCI on the monomerization rate of LPS was studied. Fluorescent (fluorescein isothiocyanate; FITC)-labeled LPS hardly exhibits fluorescence, because the micellary structure of LPS leads to the fluorescing FITC molecules being too closely packed together, giving rise to the phenomenon of fluorescence quenching. FITC-LPS Re595 (100 ng) was incubated with pure human apoCI (in molar ratios 1:1, 1:5, 1:10 and 1:20), after which the occurrence of fluorescence was followed in time with the aid of a fluorimeter. ApoCI proved to cause the increase in FITC fluorescence to increase strongly in a dose-dependent manner, which indicates that apoCI is capable of monomerizing the LPS (i.e. to liberate it from the micellary form) (FIG. 4A). By contrast, the apolipoprotein CIII (apoCIII), having a comparable size and structure, proved hardly effective (FIG. 4B).

Example 3

Plasma apoCI Binds to LPS

We have determined the effect of the apoCI level in murine plasma on monomerization of FITC-LPS as described in Example 2. For that purpose, FITC-LPS was incubated with plasma that had been isolated from wild-type mice, genetically modified mice which are deficient for apoCI (apoc1.sup.−/−), or genetically modified mice which express the human apoCI hemizygote (APOC1.sup.+/0) or homozygote (APOC1.sup.+/+).

Figure 5:
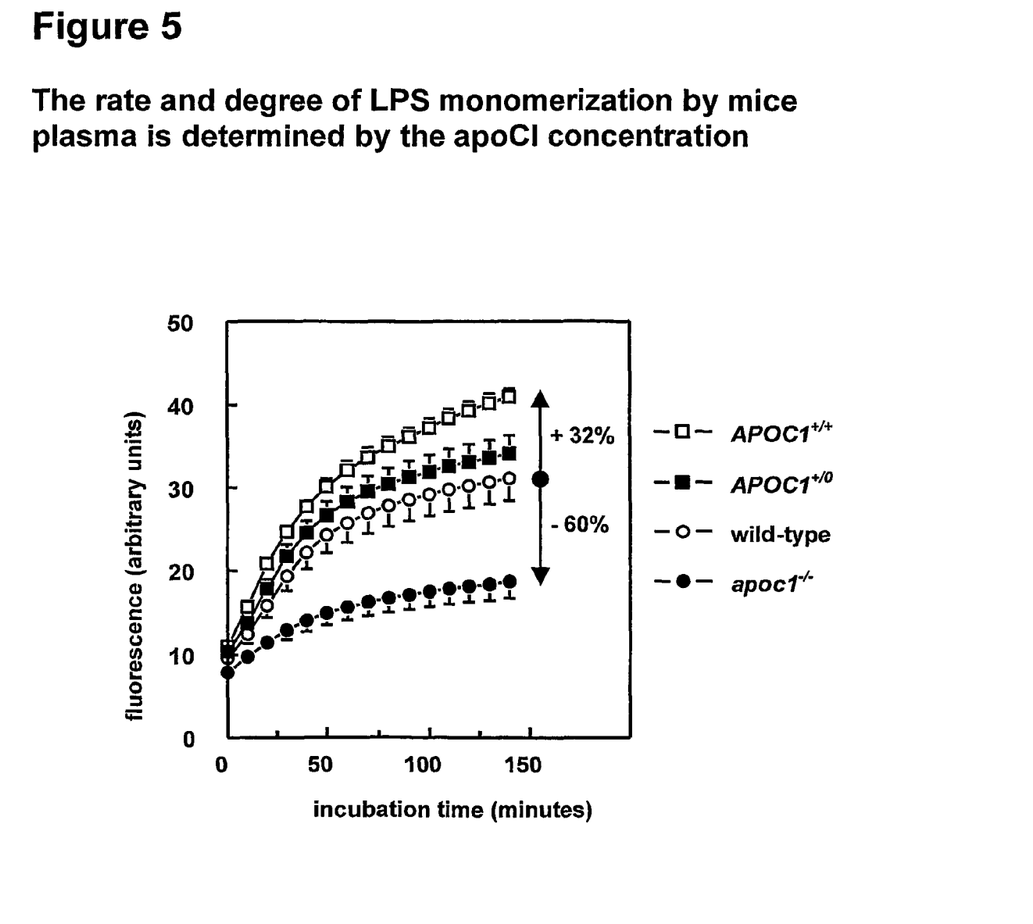
FIG. 5 shows the effect of the apoCI concentration in murine plasma on the time-dependent monomerization of LPS. The figure shows that the absence of apoCI strongly inhibits the monomerization of LPS, while expression of human apoCI increases the monomerization of LPS dose-dependently.

The results are shown in FIG. 5.

FITC-LPS Re595 (100 ng) was incubated with plasma (0.125%) isolated from the blood of the various mouse types, after which the occurrence of fluorescence was followed in time with the aid of a fluorimeter. The expression of human apoCI in mouse plasma led to an apoCI-dose dependent increase of the FITC-LPS monomerization, which was 32% at a maximum. By contrast, the monomerization of FITC-LPS proved to be reduced by 60% owing to the absence of mouse-apoCI (n=4.+−.SEM). This indicates not only that mouse-apoCI, like human apoCI, is capable of monomerizing LPS, but especially also that the endogenous presence of apoCI contributes for a considerable part to the total LPS-disaggregated capacity of mouse plasma.

Example 4

ApoCI Extends the Residence Time of LPS in the Blood by Preventing the Uptake of LPS by the Liver We have administered LPS intravenously to wild-type mice in the absence or presence of purified apoCI. Addition of apoCI proved to extend the residence time of LPS in the blood strongly through increased interaction with HDL.

Figure 6:
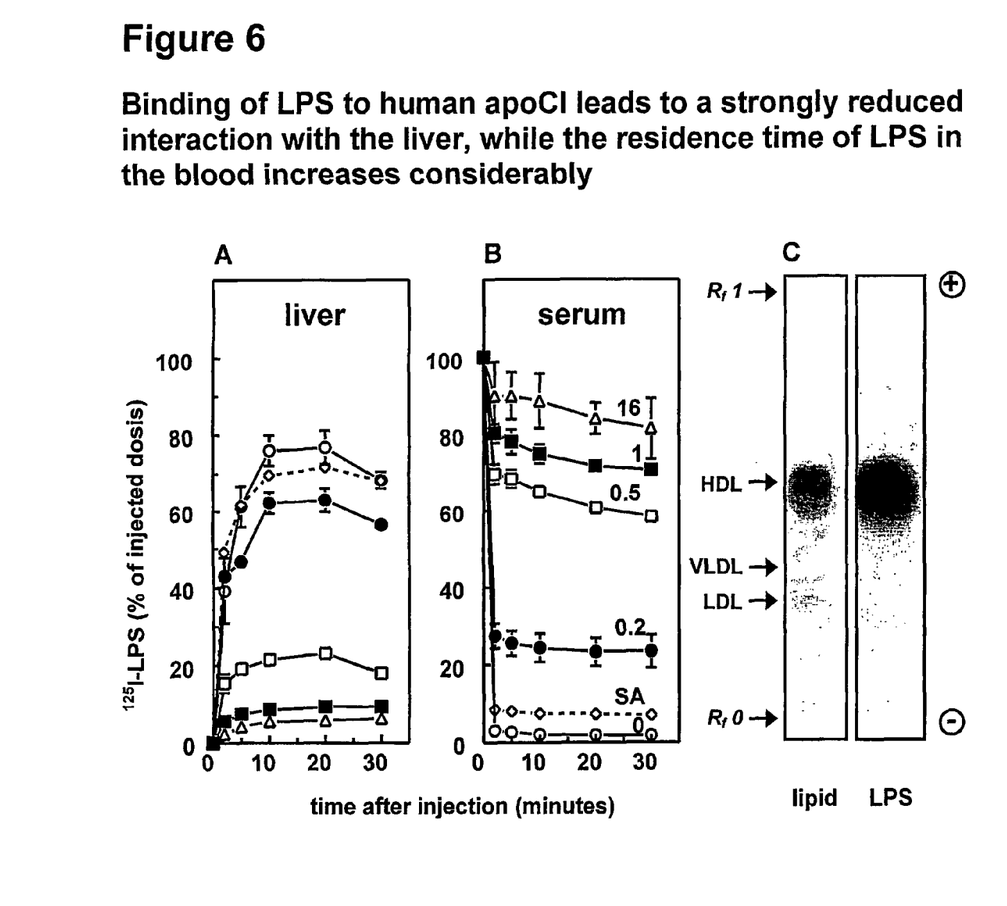
FIG. 6 shows the effect of apoCI and bovine serum albumin on the behavior of radioactively labeled LPS after intravenous injection in mice. The figure shows that apoCI is capable of strongly reducing the uptake of LPS by the liver, while the residence time of LPS in the blood increases considerably through the apoCI-induced binding of LPS to HDL. Bovine serum albumin, by contrast, proved not effective.

The results are shown in FIG. 6.

Wild-type (C57B1/6) mice were anesthetized and, via the lower vena cava, injected intravenously with radioactively (.sup.125I) labeled LPS Re595 (10 μg/kg) without, and with, respectively, apoCI (molar ratio LPS:apoCI=1:0.2, 1:0.5, 1:1 and 1:16) and bovine serum albumin (molar ratio LPS:albumin=1:16). Blood samples and bits of liver tissue were taken at t=2, 5, 10, 20 and 30 minutes after injection. After this, the mice were sacrificed. Next, the amounts of LPS in the blood sera and liver samples were quantified on the basis of the amount of radioactive radiation. Also, a serum sample was taken 30 minutes after injection of LPS:apoCI (1:1) and subjected to agarose gel electrophoresis to study the distribution of the $^{125}$I-LPS over the various lipoproteins. Lipoprotein lipids were visualized with the aid of Sudan Black, and $^{125}$I-LPS by means of autoradiography. In FIGS. 6A and 6B the amounts of $^{125}$I-LPS in the liver and the blood serum, respectively, are plotted as a percentage of the injected dose against time (n=3.+−.SEM). FIG. 6C shows the distribution of $^{125}$I-LPS over the lipoproteins. The presence of apoCI was found to inhibit the decrease of LPS from the blood strongly and dose-dependently. Already at a molar ratio of 1:1, the uptake of LPS by the liver was reduced 8-fold. The strong binding of apoCI to LPS (see Example 2) therefore proves to be relevant in the blood too. This led to an extended residence time of LPS in the blood through a strongly increased apoCI-mediated binding to HDL (FIG. 6C), thereby improving the interaction with inter alia white blood cells and eventually leading to a strongly stimulated inflammation reaction (see Example 5).

Example 5

ApoCI Stimulates the LPS-Induced Inflammatory Response in Mice

We have administered LPS intravenously to wild-type mice in the absence or presence of purified apoCI. Addition of apoCI proved to increase the LPS-induced inflammatory response strongly.

Figure 7:
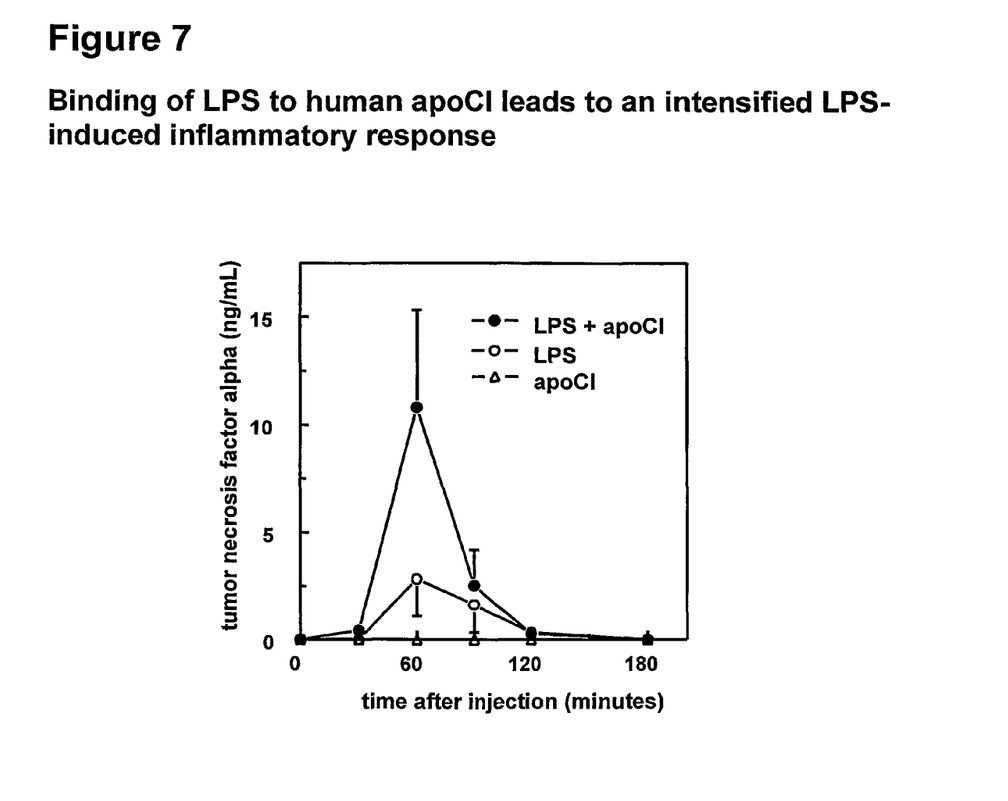
FIG. 7 shows the effect of apoCI on the LPS-induced proinflammatory response. The figure shows that the interaction of LPS with apoCI strongly increases the inflammatory response (i.e. TNFα induction).

The results are shown in FIG. 7.

Wild-type (C57B1/6) mice were injected, by way of the tail vein, with LPS Re595 (25 μg/kg) without, and with, apoCI (molar ratio LPS:apoCI=1:5). Blood samples were taken at t=0, 30, 60, 90, 120 and 180 minutes after injection. In the samples, subsequently, the amount of TNFα was quantified with the aid of a mouse-TNFα specific ELISA according to the accompanying instructions (Immunosource, Halle, Belgium, cat. no. BMS607MST), and the amounts of TNFα in the blood plasma were subsequently plotted against time. Addition of apoCI to LPS proved to lead to a fourfold increase of the LPS-induced TNF level (10.8.+−0.4.5 versus 2.8.+− 0.1.7 ng/mL), while an equal amount of apoCI without LPS has no TNFα inducing effect (n=6.+−.SEM).

Example 6

ApoCI Stimulates the LPS-Induced Inflammatory Response in Humans

We have measured the correlation between plasma apoCI levels in patients who did or did not develop endotoxemia during a heart operation with cardiopulmonary bypass, and the TNFα level during the operation. The apoCI level proved to be strongly positively correlated to the TNFα response in case of a developed endotoxemia.

Figure 8:
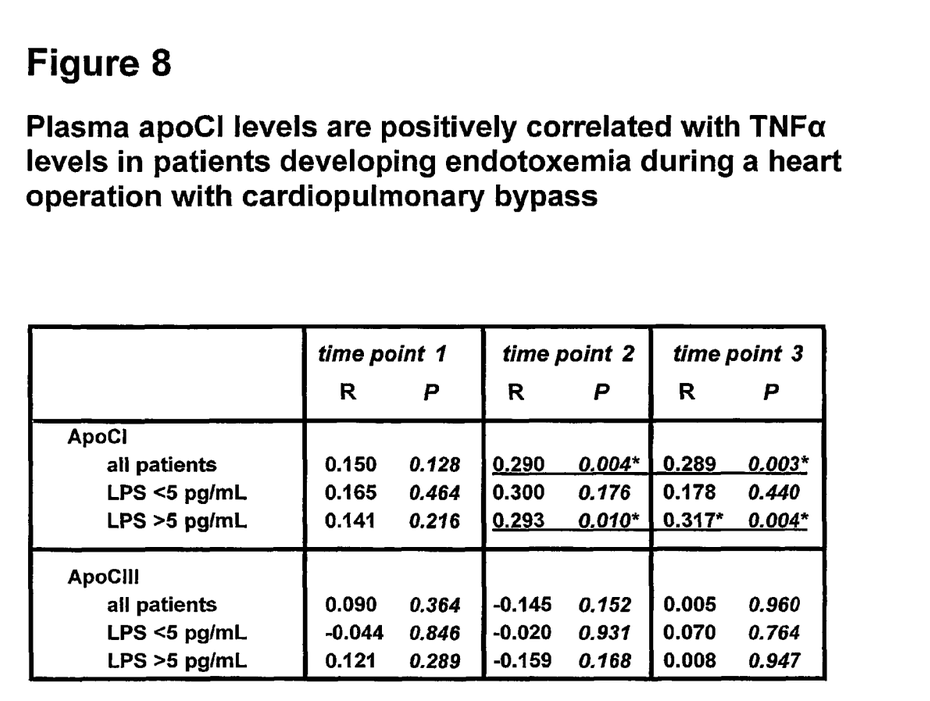
FIG. 8 shows the correlation between the apoCI levels in the plasma of patients who develop endotoxemia during a heart operation with cardiopulmonary bypass, with pre- and post-operative TNFα levels. The figure shows that there is a strongly significant positive relation between the apoCI level and the TNFα level in patients who develop endotoxemia, but not in patients who do not develop endotoxemia. Such a relation could not be demonstrated for apoCIII or apoE.

The results are shown in FIG. 8.

During a cardiopulmonary bypass, temporarily a low oxygen pressure arises in the blood which is accompanied by an endotoxemia through leakage of LPS from the intestines to the blood. We investigated the correlation between the pre-operative plasma apoCI level and the plasma TNFα level in 160 patients who had a heart operation involving a cardiopulmonary bypass. Plasma samples were taken before the operation for the purpose of measurements of lipid parameters (apoCI, apoCIII, apoE, triglycerides and total cholesterol). Also, plasma samples were taken after inducing anesthesia (time 1), after removal of the aorta clamp (time 2) and half an hour after termination of the extracorporal perfusion (time 3). At times 1, 2 and 3 the TNFα level was determined, with a distinction being made between patients who did (LPS>5 pg/mL) or did not (LPS<5 pg/mL) develop endotoxemia at both time 2 and 3. R=Spearman's rank correlation coefficient. *=statistically significant (P<0.05).

A strongly significant relation was found to exist between the apoCI level and the TNFα level in patients who during a heart operation with cardiopulmonary bypass developed endotoxemia, but not in patients who did not develop endotoxemia. Such a correlation is not demonstrated for other apolipoproteins (apoCIII, apoE) or neutral lipids (triglycerides as a measure for the amount of triglyceride-rich lipoproteins, and total cholesterol as a measure for the total amount of circulating lipoproteins), which indicates that the effect is apoCI-specific.

REFERENCES

Angus, D. C., Linde-Zwirble, W. T., Lidicker, J., Clermont, G., Carcillo, J., Pinsky, M. R. (2001) Epidemiology of severe sepsis in the United States: analysis of incidence, outcome, and associated costs of care. Crit. Care Med. 29, 1303-1310.

Barlage, S., Frohlich, D., Bottcher, A. (2001) ApoE-containing high density lipoproteins and phospholipid transfer protein activity increase in patients with a systemic inflammatory response. J. Lipid Res. 42, 281-290.

Bozza, M., Satoskar, A. R., Lin G., Lu, B., Humbles, A. A., Gerard, C., David, J. R. (1999) Targeted disruption of migration inhibitory factor gene reveals its critical role in sepsis. J. Exp. Med. 189, 341-346.

Buclin, T., Cosma Rochat, M., Burckhardt, P., Azria, M., Attinger, M. (2002) Bioavailibility and biological efficacy of a new oral formulation of salmon calcitonin in healthy volunteers. J. Bone Miner. Res. 17:1478-1485.

Calandra, T., Echtenacher, B., Roy, D. L., Pugin, J., Metz, C. N., Hultner, L., Heumann, D., Mannel, D., Bucala, R., Glauser, M. P. (2000) Protection from septic shock by neutralization of macrophage migration inhibitory factor. Nat. Med. 6, 164-170.

Clark, M. A., Plank, L. D., Connolly, A. B. et al. (1998) Effect of a chimeric antibody to tumor necrosis factor-α on cytokine and physiologic responses in patients with severe sepsis: a randomized, clinical trial. Crit. Care Med. 26, 1650-1659.

Clark-Lewis, I., Aebersold, R., Ziltener, H., Schrader, J. W., Hood, L. E., Kent, S. B. (1986) Automated chemical synthesis of a protein growth factor for hemopoietic cells, interleukin-3. Science 231, 134-139.

Cohen, J., Glauser, M. P. (1991) Septic shock: treatment. Lancet 338, 736-739.

Cohen, J. (1999) Adjunctive therapy in sepsis: a critical analysis of the clinical trial programme. Br. Med. Bull. 55, 212-225.

Cronin, L., Cook, D. J., Carlet, J. et al. (1995) Corticosteroid treatment for sepsis: a critical appraisal and meta-analysis of the literature. Crit. Care. Med. 23, 1430-1439.

Curry, M. D., McConathy, W. J., Fesmire, J. D., and Alaupovic, P. (1981) Quantitative determination of apolipoproteins C-I and C-II in human plasma by electroimmunoassays. Clin. Chem. 27, 543-548.

Fisher, C. J., Dhainaut, J. F., Opal, S. M. (1994) Recombinant human interleukin 1 receptor antagonist in the treatment of patients with sespsis syndrome: results from a randoized double-blind, placebo-controlled trial. JAMA 271, 1836-1843.

Fisher, C. J., Agosti, J. M. Opal, S. M. et al. (1996) Treatment of septic shock with the tumor necrosis factor receptor:Fc fusion protein. The Soluble TNF Receptor sepsis study Group. N. Engl. J. Med. 334, 1697-1702.

Heumann, D., Roger, T. (2002) Initial responses to endotoxins and Gram-negative bacteria. Clin. Chim. Acta 323, 59-72.

Hoess, A., Watson, S., Siber, G. R., Liddington, R. (1993) Crystal structure of an endotoxin-neutralizing protein from the horseshoe crab, Limulus anti-LPS factor, at 1.5.ANG. resolution. EMBO J. 12, 3351-3356.

Jackson, R. L., Holdsworth, G. (1986) Isolation and properties of human apolipoproteins C-I, C-II, and C-III. Methods Enzymol. 128, 288-297.

Jong, M. C., Dahlmans, V. E. H., Van Gorp, P. J. J. et al. (1996) In the absence of the low density receptor, human apolipoprotein C1 overexpression in transgenic mice inhibits the hepatic uptake of very low density lipoproteins via a receptor-associated protein-sensitive pathway. J. Clin. Invest. 98, 2259-2267.

Jong, M. C., Gijbels, M. J. J., Dahlmans, V. E. H. et al. (1998) Hyperlipidemia and cutaneous abnormalities in transgenic mice overexpressing apolipoprotein C1. J. Clin. Invest. 101, 145-152.

Jong, M. C., Hofker, M. H., Havekes, L. M. (1999) Role of apoCs in lipoprotein metabolism: functional differences between apoCI, apoC2, and apoC3. Artherioscler. Thromb. Vasc. Biol. 19, 472-484.

Koebernick, H. et al. (2002) Macrophage migration inhibitory factor (MIF) plays a pivotal role in immunity against *Salmonella typhimurium*. Proc. Natl. Acad. Sci. USA 99, 13681-13686.

Kiechl, S. Lorenz, E., Reindl, M., Wiedermann, C. J., Oberhollenzer, F., Bonora, E., Willeit, J., Schwartz, D. A. (2002) Toll-like receptor 4 polymorphisms and atherogenesis. N. Engl. J. Med. 347, 185-192.

Kypreos, K. E., Willems van Dijk, K., Van der Zee, A., Havekes, L. M., Zannis, V. I. (2001) Domains of apolipoprotein E contributing to triglyceride and cholesterol homeostasis in vivo. J. Biol. Chem. 276, 19778-19786.

Larrick, J. W., Hirata, M., Zheng, H. et al. (1994) A novel granylocyte-derived peptide with lipopolysaccharide-neutralizing activity. J. Immunol. 152, 231-240.

Opal, S. M., Fisher, C. J., Dhainaut, J. F. et al. (1997) Confirmatory interleukin-1 receptor antagonist trial in severe sepsis: a phase III, randomized, double-blind, placebo-controlled, multicenter trial. The Interleukin-1 Receptor Antagonist Sepsis Investigator Group. Crit. Care Med. 26, 1115-1124.

Rackow, E. C., Astiz, M. E. (1991) Pathophysiology and treatment of septic shock. JAMA 266, 548-554.

Rensen, P. C. N., Van Oosten, M., Van de Bilt, E. et al. (1997) Human apolipoprotein E protects redirects lipopolysaccharide from Kupffer cells to liver parenchymal cells in rats in vivo. J. Clin. Invest. 99, 2438-2445.

Satoskar, A. R., Bozza, M., Rodriquez Sosa, M., Lin, G., David, J. R. (2001) Migration-inhibitory factor gene-deficient mice are susceptible to cutaneous *Leishmania major* infection. Infect. Immun. 69, 906-911.

Tournier, J. F., Bayard, F., Tauber, J. P. (1984) Rapid purification and activity of apolipoprotein C.sub.I on the proliferation of bovine vascular endothelial cells in vitro. Biochim. Biophys. Acta 804, 216-220.

Van der Poll, T., Braxton, C. C., Coyle, S. M. et al. (1995) Effect of hypertriglyceridemia on endotoxin responsiveness in humans. Infect. Immun. 63, 3396-3400.

Wheeler, A. P., Bernard, G. R. (1999) Treating patients with severe sepsis. N. Engl. J. Med. 340, 207-214.

The invention claimed is:

1. A method for treating a mammal suffering from or at risk of developing sepsis or septic shock comprising administering to such mammal a therapeutically effective amount therefor of a peptide and pharmaceutically acceptably adjuvants, wherein the peptide has an amino acid sequence comprising: (A) SEQ ID NO.:2 or (B) a fragment of SEQ ID NO.:2 that comprises SEQ ID NO.:11.

2. The method according to claim 1, wherein the mammal is at risk of developing sepsis as a result of a surgical intervention or a weakened immune system.

3. The method according to claim 1, wherein the peptide binds to lipoteichoic acids.

4. The method according to claim 1, wherein the shock is caused by Gram-negative bacteria.

5. The method according to claim 4, wherein the mammal is a human, horse, cow, dog or cat.

6. The method according to claim 1, wherein the shock is caused by Gram-positive bacteria.

7. The method according to claim 6, wherein the mammal is a human, horse, cow, dog or cat.

8. The method according to claim 1, wherein the mammal is a human.

9. The method of claim 1, wherein the peptide comprises the amino acid sequence of SEQ ID NO.:1.

10. The method of claim 1, wherein the peptide comprises SEQ ID NO.:2.

11. The method of claim 1, wherein the peptide is the amino acid sequence of SEQ ID NO.:2.

12. The method of claim 11, wherein the mammal is a human.

13. The method of claim 1, wherein the peptide is an amino acid sequence selected from the group consisting of: SEQ ID NO.:11, SEQ ID NO.:2 and SEQ ID NO.:1.

14. The method according to claim 1, wherein the peptide is administered as a free peptide, not complexed with lipids.

15. The method according to claim 13, wherein the peptide is administered as a free peptide, not complexed with lipids.

* * * * *